United States Patent [19]
White et al.

[11] Patent Number: 5,284,648
[45] Date of Patent: Feb. 8, 1994

[54] ALCOHOL-FREE, ORAL RINSE AND PRE-RINSE EMULSIONS METHOD OF PREPRATION AND METHOD OF USE

[76] Inventors: Robert D. White, 65 Glen Grey Ct., Oakland, N.J. 07436; Ira D. Hill, Clay Ct., Locust, N.J. 07760

[21] Appl. No.: 776,055

[22] Filed: Oct. 15, 1991

Related U.S. Application Data

[63] Continuation-in-part of Ser. No. 324,894, Mar. 17, 1989, abandoned, and a continuation-in-part of Ser. No. 325,216, Mar. 17, 1989, abandoned, and a continuation-in-part of Ser. No. 326,179, Mar. 17, 1989, abandoned.

[51] Int. Cl.$^5$ .................... A61K 7/16; A61K 7/18; A61K 7/22; A61K 7/26
[52] U.S. Cl. .................... 424/49; 424/52; 424/54; 424/57; 424/58
[58] Field of Search .................... 424/49–58

[56] References Cited

U.S. PATENT DOCUMENTS

| | | | |
|---|---|---|---|
| 2,422,145 | 6/1947 | Taylor | 99/140 |
| 2,508,978 | 5/1950 | Tribble | 99/140 |
| 2,566,410 | 9/1951 | Griffin | 99/140 |
| 2,806,814 | 9/1957 | Richter | 167/93 |
| 3,507,955 | 4/1970 | Osipow | 424/54 |
| 3,624,120 | 11/1971 | Yetter | 260/448.2 |
| 3,639,563 | 4/1972 | Januszewski | 424/49 |
| 3,666,496 | 5/1972 | Honey et al. | 99/140 R |
| 3,674,502 | 4/1972 | Honey et al. | 99/28 |
| 3,729,553 | 4/1973 | Gold et al. | 424/44 |
| 3,833,743 | 9/1974 | Morse et al. | 426/195 |
| 3,876,759 | 4/1975 | Pensak et al. | 424/58 |
| 3,947,567 | 3/1976 | Berg, Jr. et al. | 424/45 |
| 3,947,570 | 3/1976 | Pensak et al. | 424/54 |
| 4,011,309 | 3/1977 | Lutz | 424/52 |
| 4,132,770 | 1/1979 | Barth | 424/49 |
| 4,343,785 | 8/1982 | Schmolka | 424/49 |
| 4,420,471 | 12/1983 | Elton et al. | 424/49 |
| 4,465,661 | 8/1984 | Schmolka | 424/49 |
| 4,476,107 | 10/1984 | Schmolka | 424/49 |
| 4,510,127 | 4/1985 | Chang | 424/52 |
| 4,525,342 | 6/1985 | Chang | 424/49 |
| 4,537,778 | 8/1985 | Clipper et al. | 424/53 |
| 4,550,018 | 10/1985 | Ambike et al. | 424/52 |
| 4,657,758 | 4/1987 | Goldemberg et al. | 424/49 |
| 4,666,708 | 5/1987 | Goldemberg et al. | 424/49 |
| 4,684,517 | 8/1987 | Clipper et al. | 424/52 |
| 4,919,918 | 4/1990 | Cole et al. | 424/44 |
| 4,923,685 | 5/1990 | Wuelknitz et al. | 424/54 |
| 4,950,479 | 8/1990 | Hill et al. | 424/49 |
| 4,971,785 | 11/1990 | Wilson et al. | 424/44 |
| 5,009,881 | 4/1991 | Hill et al. | 424/49 |
| 5,032,387 | 7/1991 | Hill et al. | 424/49 |
| 5,057,306 | 10/1991 | Hill et al. | 424/49 |
| 5,057,307 | 10/1991 | Hill et al. | 424/49 |
| 5,057,309 | 10/1991 | Hill et al. | 424/52 |
| 5,078,988 | 1/1992 | Lin et al. | 424/49 |

FOREIGN PATENT DOCUMENTS 689679 10/1951 United Kingdom .

*Primary Examiner*—Shep K. Rose
*Attorney, Agent, or Firm*—Robert D. White; Ira D. Hill

[57] ABSTRACT

The invention relates to alcohol-free, oral pre-rinse and rinse emulsions containing cleaning and coating compositions that are non-irritating and low foaming thus allowing a residence time sufficient to condition teeth and gums and disruptively affect the plaque matrix. Such disruption allows for the reduction of plaque build-up by either of two efficacious and convenient mechanisms: (1) immediate removal of disrupted plaque matrix by normal brushing or (2) interruption of plaque forming activity in the mouth by frequently cleaning out plaque and plaque precursors, coupled with reduced attachment of plaque by altering the tooth surfaces with the coating compositions.

41 Claims, No Drawings

ALCOHOL-FREE, ORAL RINSE AND PRE-RINSE EMULSIONS METHOD OF PREPRATION AND METHOD OF USE

CROSS-REFERENCE TO RELATED APPLICATIONS

This application is a continuation-in-part of the following copending applications:
Ser. No. 07/324,894—filed Mar.17, 1989, entitled Alcohol-Free Pre-Rinse, now abandoned,
Ser. No. 07/325,216—filed Mar. 17, 1989, entitled Method of Treating the Oral Cavity, now abandoned, and
Ser. No. 07/326,179—filed Mar. 17, 1989, entitled Method of Manufacturing An Alcohol-Free Pre-Rinse Emulsion, no abandoned, the disclosures of which are hereby incorporated herein by reference.

The subject matter disclosed and/or claimed herein is also related to the subject matter of other patents and/or patent applications by the present inventors. These include:
Ira Hill & Robert White 06/927,805 Filed: Nov. 6, 1986 METHOD OF INTERRUPTING THE FORMATION OF PLAQUE now, U.S. Pat. No. 4,950,479;
Ira Hill & Robert White 06/927,752 Filed: Nov. 6, 1986 DENTAL AND ORAL HYGIENE PREPARATIONS now, U.S. Pat. No. 5,032,387;
Ira Hill & Robert White 07/270,165 Filed: Nov. 14, 1988 DENTAL STIMULATOR now, U.S. Pat. No. 4,942,034;
Ira Hill & Robert White 07/270,544 Filed: Nov. 14, 1988 DENTAL FLOSS now, abandoned;
Ira Hill & Robert White 07/453,302 Filed: Dec. 20, 1989 DENTAL FLOSS WITH CHEMOTHERAPEUTIC AGENTS now, pending;
Ira Hill & Robert White 07/270,562 Filed: Nov. 14, 1988 METHOD AND APPARATUS FOR ADDING CHEMOTHERAPEUTIC AGENTS TO DENTAL FLOSS now, U.S. Pat. No. 4,911,927;
Ira Hill & Robert White 07/270,162 Filed: Nov. 14, 1988 METHOD OF TREATING THE ORAL CAVITY WITH DENTAL FLOSS now, abandoned;
Ira Hill & Robert White 07/452,829 Filed: Dec. 20, 1989 METHOD OF TREATING THE ORAL CAVITY WITH DENTAL FLOSS CONTAINING CHEMOTHERAPEUTIC AGENTS now, pending;
Ira Hill & Robert White 07/270,163 Filed: Nov. 14, 1988 DENTAL FLOSS WITH TETRACYCLINE now, abandoned;
Ira Hill & Robert White 07/270,723 Filed: Nov. 14, 1988 DENTAL FLOSS WITH STABILIZED STANNOUS FLUORIDE now, abandoned;
Ira Hill & Robert White 07/270,132 Filed: Nov. 14, 1988 DENTAL FLOSS WITH CHLORHEXIDINE now, abandoned;
Ira Hill & Robert White 07/270,167 Filed: Nov. 14, 1988 DENTAL FLOSS WITH SODIUM FLUORIDE now, abandoned;
Ira Hill & Robert White 07/270,135 Filed: Nov. 14, 1988 DENTAL FLOSS WITH POLYVINYL PYROLLIDONE COMPLEX OF IODINE now, abandoned;
Ira Hill & Robert White 07/270,161 Filed: Nov. 14, 1988 METHOD OF TREATING THE ORAL CAVITY WITH DENTAL FLOSS CONTAINING TETRACYCLINE now, abandoned;
Ira Hill & Robert White 07/270,353 Filed: Nov. 14, 1988 METHOD OF TREATING THE ORAL CAVITY WITH DENTAL FLOSS WITH STANNOUS FLUORIDE now, abandoned;
Ira Hill & Robert White 07/270,166 Filed: Nov. 14, 1988 METHOD OF TREATING THE ORAL CAVITY WITH DENTAL FLOSS WITH CHLORHEXIDINE now, abandoned;
Ira Hill & Robert White 07/270,164 Filed: Nov. 14, 1988 METHOD OF TREATING THE ORAL CAVITY WITH DENTAL FLOSS CONTAINING POLYVINYL PYROLLIDONE IODINE COMPLEX now, abandoned;
Ira Hill & Robert White 07/325,216 Filed: Mar. 17, 1989 METHOD OF TREATING THE ORAL CAVITY now, pending;
Ira Hill & Robert White 07/324,894 Filed: Mar. 17, 1989 ALCOHOL-FREE PRE-RINSE EMULSION now, pending;
Ira Hill & Robert White 07/535,499 Filed: Jun. 8, 1990 ORAL HYGIENE GELS now, U.S. Pat. No. 5,009,881
Ira Hill & Robert White 07/535,920 Filed: Jun. 8, 1990 METHOD OF RELIEVING GUM DISCOMFORT now, pending;
Ira Hill & Robert White 07/535,912 Filed: Jun. 8, 1990 METHOD OF MANUFACTURING ORAL HYGIENE GELS now, pending;
Ira Hill & Robert White 07/535,911 Filed: Jun. 8, 1990 ORAL HYGIENE PREPARATIONS now, pending;
Ira Hill & Robert White 07/535,913 Filed: Jun. 8, 1990 METHOD OF TREATING THE ORAL CAVITY WITH ORAL HYGIENE PREPARATIONS CONTAINING ACTIVE $SnF_2$ now, pending;
Ira Hill & Robert White 07/534/922 Filed: Jun. 8, 1990 METHOD OF MANUFACTURING ORAL HYGIENE PREPARATIONS CONTAINING ACTIVE $SnF_2$ now, pending.

BACKGROUND OF THE INVENTION

Dental plaque is present to some degree, in the form of a film; i.e., pellicle, on virtually all dental surfaces. It is a by-product of microbial growth, and comprises a dense microbial layer consisting of a mass of microorganisms embedded in a polysaccharide matrix. The microorganisms present in plaque are mainly coccoidal organisms, particularly in early, soft plaque, which, in the mouths of some persons at least, change to filamentous organisms after a few days. Plaque itself adheres firmly to dental surfaces and is removed only with difficulty even through a rigorous brushing regimen. Moreover, plaque rapidly reforms on the tooth surface after it is removed.

A wide variety of microorganisms are found in the oral cavity, and among these are gram-positive anaerobic rods associated with the development of plaque such as *Corynebacterium. Nocardia* and *Neisseria* streptococci, such as *S. mutans. S. bovis, S. salivarius*. Gram-positive streptococci of the genus *Peotostreotococcus* have also been identified (see, Robert J. Fitzgerald in *The Alabama Journal of Medical Sciences*. Vol. 5, No. 3, Jul., 1968, pp. 241-242).

The above mentioned microorganisms play a key role in the etiology of plaque. The bacterial organisms associated with plaque formation produce a capsular material which apparently causes the cells of the organism to adhere to each other, holding the plaque together and allowing for further growth. For example, one of the capsule forming bacteria which occurs in large numbers in early plaque is *Neisseria sicca*. In addition to the aforementioned microorganisms, there is also present in plaque relatively small amounts of other substances such as salivary proteins, carbohydrates, epithelial cells and leukocytes.

Plaque may form on any parts of the tooth surface, and is found particularly at the gingival margin, in cracks in the enamel, and on the surface of the dental calculus. As discussed in greater detail below, the danger associated with the formation of plaque on the teeth lies in the tendency of plaque to build up and eventually produce gingivitis, periodontitis and other types of periodontal disease, as well as dental caries and dental calculus.

More specifically, dental plaque is a precursor to the formation of the hard crystalline buildup on teeth referred to as dental calculus. Both the bacterial and the nonbacterial components of plaque mineralize to form calculus, which comprises mineralized bacteria as well as organic constituents, such as epithelial cells, live bacteria, salivary proteins, leukocytes, and crystals of substances having molecularly bound calcium and phosphorus, e.g., hydroxyapatite, $3Ca_3(PO_4)_2 \cdot Ca(OH)_2$, octacalcium phosphate, $Ca_8(HPO_4)_2(PO_4)_4 \cdot 5H_2O$, brushite, $CaHPO_4 \cdot 2H_2O$, and whitlockite, which is considered to have the form of a beta-$Ca_3(PO_4)_2$.

Dental plaque and, hence, calculus are particularly prone to form at the gingival margin, i.e., the junction of tho tooth and gingiva. The buildup of plaque at the qingival margin is believed to be the prime cause of gingivitis and other periodontal disorders.

Regular tooth brushing with a conventional dentifrice for some persons greatly retards or even prevents the accumulation of significant amounts of plaque and calculus. For other persons, however, plaque builds up rapidly even with regular brushing which, in turn. leads to the formation of calculus, caries, and presents the danger of periodontal diseases. Removal of plaque and-/or calculus by a dentist is currently the only safeguard against serious gingival inflammation caused by the accumulation of significant amounts of plaque in some individuals. It is widely recognized in dentistry that a rigorous brushing regimen alone for many individuals will not prevent the formation of significant amounts of plaque.

Mouthwashes are employed in conventional regimens of oral hygiene. However, conventional mouthwashes serve primarily to sweeten the breath, are formulated for that purpose, and are believed not to function in any significant way to loosen or remove plaque from the dental surfaces. Moreover, since the user typically does not employ a mouthwash expressly for the purpose of cleansing the teeth of plaque, mouthwashes are not routinely used immediately prior to brushing as a way of rendering plaque and/or calculus more amenable to removal during the subsequent brushing process.

Most mouthwashes and pre-rinses contain alcohol and other antimicrobial substances which may alter the critically balanced microflora of the mouth. Generally, these alcohol containing preparations cannot be used on sensitive or irritated gums nor safely by children or those individuals recovering from alcohol abuse. Moreover, the alcohol content in these preparations usually restricts the practical requirement of sufficient contact time in the mouth due to the irritation of the oral mucosa. Most rinse and pre-rinse preparations include instructions advising the consumer to swish the product in the mouth for about 60 seconds. The pain and mucosa irritation due primarily to alcohol astringency is often so intense that most rinse and pre-rinse users actually expectorate in only a few seconds which is usually followed by a water rinse. This relatively short residence time followed by water rinsing dramatically reduces any mouth cleansing and/or plaque fighting effect that these preparations might have.

Most oral rinses sold commercially today contain alcohol in concentrations ranging from between about 5 and about 27% by weight. These high alcohol concentrations impart microbial stability to these rinses. These antiseptic rinses also usually contain other antimicrobial substances such as phenolics, thymol, eucalyptol, cetylpyridinium chloride, sodium benzoate, sanguanarine root, etc., at levels far beyond that required for preservation during storage. The cleaner concentrations generally range from 0.1 to about 0.25%, and generally less than 1.0%. Most rinses make various claims ranging from germ kill, cavity fighting and plaque or tartar control to breath freshening, but few address the critical issue; cleaning the oral cavity.

Various types of commercial oral rinses are employed in diverse regimens of oral hygiene. These include:

a. Conventional mouthwashes which serve primarily to sweeten the breath with volatile flavor odors and are not formulated to function in any significant way to cleanse the mouth of debris and/or to loosen or remove plaque from dental surfaces.

b. Pre-rinse formulations, used immediately prior to brushing as a way of rendering plaque and/or calculus more amenable to removal during the subsequent brushing process. See for example, U.S. Pat. No. 4,657,758, and c. Gingivitis and/or tartar control rinses containing antimicrobials such as phenols, sanguinaria, chlorhexidine and stannous fluoride; and antitartar or plaque fighters such as sodium or potassium pyrophosphates and sodium benzoate. Some of these are described in the review by K. S. Kornman, *Dent. Placue Control Meas. Oral Hyg. Pract. Proc.*, pp. 121–142 (1986).

All of these commercial rinses are characterized by a relatively high alcohol content and antimicrobial and-/or antiseptic activity that disrupts the critically balanced microflora of the mouth. This alcohol content also provides the rinse a microbially stable formulation, which does not support the growth of microorganisms, and allows the rinse to be stored for prolonged periods and/or used without concern for microbial contamination. The alcohol also serves to reduce the foamability of the rinse. However, this foaming control is limited to relatively low surfactant concentrations in the rinse. Finally, alcohol also functions as a solvent for the flavor oils typically included in commercial rinses.

There are inherent limitations in the use of alcohol containing oral rinses. For example, most adults will experience some form of gum irritation, on average about once a year. This irritation ranges from sites of early gingivitis, canker sores and trench mouth to periodontal disease. At such times, alcohol rinses cause even greater pain and are often replaced by rinsing with water.

Alcohol containing rinses and/or pre-rinses are generally not used by children. Most parents are concerned about the alcohol content, while many children reject the alcohol bite and astringency characteristic of such products. Indeed, most alcohol containing rinses and/or pre-rinses boldly display the language "Keep Away From Children" on their labels. Similarly large numbers of adults reject alcohol based rinses for various personal reasons. Additionally, recovering alcoholics avoid alcohol rinses because of the threat that these substances can trigger a negative response. For example, most institutionalized personnel are not allowed to use alcohol based rinses.

There is, therefore, a definite need in the art for an oral hygiene composition which is microbially stable, alcohol-free and non-irritating; that can be used as an oral rinse or pre-rinse to clean and condition the teeth and gums, cleanse the mouth of debris and disrupt plaque matrix formation, without substantially altering the microflora balance of the oral cavity.

In view of the foregoing, it is an object of this invention to provide an improved dental rinse which is non-irritating and which has a disruptive cleaning effect upon plaque; which conditions the teeth and gums and which clears the mouth of debris, and disrupts plaque matrix formation, all without altering the balanced microflora of the oral cavity; wherein the rinse is alcohol-free yet microbiologically stable.

It is also an object of this invention to provide an improved method of oral hygiene, i.e., the method of disrupting plaque, clearing the mouth of debris, conditioning teeth and gums without altering the microflora balances of the oral cavity, which entails using the alcohol-free rinse of the present invention.

It is a further object of this invention to provide an improved process for manufacturing an alcohol-free dental rinse.

SUMMARY OF THE INVENTION

In accordance with the foregoing objectives, this invention provides: (1) an alcohol-free, microbially stable, non-irritating, oral rinse emulsion that disruptively cleans plaque; clears the mouth of debris and conditions both the teeth and gums without disrupting the critically balanced microflora of the oral cavity. This emulsion comprises one or more members selected from a specific class of surfactants and a one or more members selected from a specific class of coating materials, wherein the coating material is emulsified in the surfactant.

For the purposes of the present invention, the term "alcohol-free" is defined such that the rinse formulation of the present invention is substantially free, and most preferably, completely free of ethanol. More specifically, the present rinse formulation does not exhibit the astringency and/or bite generally characteristic of alcohol based rinses, nor does the present formulation carry with it the negative connotations presently associated with alcohol containing materials. Recently, there have been concerns expressed in the various media (print and television) as to the carcinogenicity (e.g., oral cancers) of alcohol in various mouthwash and oral care products.

For the purposes of the present invention, the term "microbially stable" is defined such that the rinse formulation of the present invention does not support microbiological activity, particularly as shown in Examples 14 and 15 of Table I below.

For the purposes of the present invention, the term "non-irritating" is defined as perceptibly non-irritating to the oral mucosa. That is, the rinse formulation of the present invention can be introduced into the oral cavity and swished therein for about at least 50 seconds, comfortably, with no noticeable discomfort, pain or bite and with no need to rinse the oral cavity with water after expectorating the rinse. See the discussion of the Examples set out in Tables I and IV below.

For the purposes of the present invention, an emulsion is defined as a non-separating mixture of two or more immiscible liquid phases with the continuous phase comprising water and the discontinuous phase(s) being one or more mutually insoluble and water insoluble liquids. For the purpose of the present invention, "emulsion" includes micells and those mixtures obtained with high shear mixing under "hot melt" emulsion processing as described in the preparation of Examples 1–15 below. Preferred emulsions of the present invention are stable under one or more freeze-thaw cycles.

For the purposes of the present invention, the "critically balanced microflora of the oral cavity" is defined as the ecologically stable mixture microflora normally found in the oral cavity in the absence of alcohol, antimicrobials, antiseptic substances, etc. For the purposes of the present invention, the effects of clearing debris, disruptively cleaning plaque and conditioning surfaces in the oral cavity are not considered disruptive to the balanced microflora. The reduction of total microflora population does not appreciably alter the relative balance of the microflora.

For the purposes of the present invention, a disruptive plaque cleaning effect is obtained with the introduction into the oral cavity of a surfactant coating emulsion in a non-irritating alcohol-free pre-rinse that coats and penetrates the plaque matrix with a plaque softening and disrupting mixture.

For the purposes of the present invention, the term "Oral Cavity Residence Factor" (OCRF) is defined as the product of length of time the pre-rinse or rinse can be swished about the oral cavity without irritation, discomfort and the need to subsequently flush the oral cavity with water. The residence time should be sufficient to achieve disruption of the plaque matrix with the pre-rinse or rinse of the present invention and condition the surfaces of the oral cavity.

Pre-rinsing residence time is generally greater than 30 seconds and usually up to about 60 seconds. See Table IV (below).

For the purposes of the present invention, plaque matrix disruption is defined as the condition of the plaque matrix after pre-rinsing for the pre-rinsing residence time and comprises the plaque matrix containing surfactant and conditioner. This disrupted plaque matrix is more effectively removed with subsequent mechanical brushing than a non-disrupted plaque matrix.

For the purposes of the present invention, a mouth conditioner is defined as a coating composition that is emulsified in the surfactant which leaves the surfaces of the oral cavity feeling smooth during the pre-rinsing residence time and conditions the oral cavity sufficient to allow pre-rinsing and to extend for the pre-rinsing residence time without irritation discomfort or the need for a subsequent rinse. In the absence of subsequent brushing, the conditioned surfaces of the oral cavity will continue to feel smooth and "just brushed" for up to about 30 minutes.

For the purposes of the present invention, low-foaming is defined as a property in which the quantity of foam generated by vigorous swishing in the mouth, does not:
- a. interfere with the continued swishing action required i.e., up to 60 seconds,
- b. does not fill the mouth to an unpleasant level, and
- c. does not interfere with effective liquid contact with tooth and mouth surfaces.

For the purposes of the present invention, the term "pre-rinse" is defined as a rinsing agent (or action) employed just prior (hence "pre-") to normal brushing with a tooth brush and dentifrice, while the term "rinse" is a similar agent (or action) not immediately followed by brushing. For brevity herein, the invention will be described as a "pre-rinse" but such use is intended to include "rinse" formulations as well.

For the purposes of the present invention, mouth conditioner is defined as a coating composition as described hereinafter.

It has now been found that when certain cleaning and coating compositions described below are incorporated into alcohol-free mouth pre-rinses they disrupt the plaque matrix and disrupt plaque reattachment and;
- a. condition gums and teeth,
- b. coat surfaces of the mouth with a lasting, plaque disrupting coating and cleaning mixtures that is ingestible,
- c. clear the mouth of debris,
- d. impart a lasting smooth, clean, just-brushed feeling to the mouth,
- e. are low-foaming and ingestible,
- f. disrupt the plaque matrix and control plaque formation without killing germs and/or altering the microflora of the mouth,
- g. are particularly effective in conditioning sensitive and irritated gums, and
- h. can be safely used as children's rinses; not only because they are alcohol free but also because the cleaner/coating compositions of the invention can be ingested and thus are not harmful if accidentally swallowed by a child.

In a preferred embodiment of this invention, the oral pre-rinse or rinse emulsion comprises a microbially stable aqueous emulsion of water, surfactant and silicone. This emulsion can appear clear or opaque when viewed in a standard four to 16 oz. plastic or glass bottle.

In further preferred embodiments of the dental rinse of this invention, effective amounts of flavor, sweeteners, humectants, desensitizing agents, viscosity control agents, antioxidants and buffering ingredients may be used.

The oral pre-rinse of this invention may be applied to the surface of the teeth by any conventional process. Preferably however, the dental pre-rinse is applied by placing a comfortable amount of the dental pre-rinse in the oral cavity (e.g., about 10 to 15 ml) and then circulating the pre-rinse about the mouth with the intention of thoroughly soaking the teeth and gums.

The disruptive effect attributed to the oral pre-rinses of this invention is due in part of the high concentrations of certain surfactant compositions containing emulsified coating compositions. These surfactants are melted and the coating compositions are emulsified into this melt, usually with high shear. This melt-emulsion, in a liquid state, accepts and emulsifies other non-solubles such as flavor oils, etc., as additional discontinuous phases. While still molten, this melt emulsion is added to the water phase of the rinse to produce a microbiologically stable, alcohol-free, non-irritating pre-rinse (or rinse) preparation.

The dramatic mouth clearing, disruption of plaque matrix and conditioning of teeth and gums accomplished through the use of the oral pre-rinse preparations of the invention should also serve both to reduce dental caries closely associated with plaque buildup, as well as preventing or ameliorating plaque and plaque associated oral disorders such as gingivitis and periodontitis.

Further advantages and objectives of this invention will be apparent from the detailed description of the invention which follows.

DETAILED DESCRIPTION OF THE PREFERRED EMBODIMENTS

The oral pre-rinse preparations of this invention comprise an alcohol-free, microbially stable, non-irritating emulsion of surfactants and coating substances that disruptively affect plaque, cleanse the mouth of debris and condition gums without disrupting the critically balanced microflora of the oral cavity. The surfactant and coating substances are incorporated into these aqueous based preparations as "hot-melt" emulsions in concentrations from between about 1 and 4 percent by weight and from between about 0.001 and about 0.5 percent by weight respectively.

The cleaners of the invention include: surfactants and emulsifiers such as:
polyethylene glycol stearate,
polyethylene glycol monostearate,
coconut monoglyceride sulfonates,
alkyl polyglycol ether carboxylates such as those described in U.S. Pat. No. 4,130,636
polyoxyethylene derivatives of sorbitan esters, such as those described in U.S. Pat. Nos. 3,639,563; 3,947,570,
propoxylated cetyl alcohol, such as those described in U.S. Pat. No. 2,677,700.

Preferred commercially available substances which include:
polyoxyethylene, polyoxybutylene block copolymers such as Pluronic F108, and F127 (BASF) and polysorbates such as Tween 40, and 80 (Hercules).

Particularly preferred surfactants include block copolymers comprising a cogeneric mixture of conjugated polyoxybutylene and polyoxyethylene compounds having as a hydrophobe, a polyoxybutylene polymer of at least 1200 molecular weight; such as those described in U.S. Pat. Nos. 4,343,785, 4,465,663, 4,511,563 and 4,476,107.

The coating substances can be characterized as follows, they:
1. suppress the tendency of the surfactant cleaners that are present to foam,
2. are safely ingestible at the concentrations used,
3. have an affinity for mouth and teeth surfaces,
4. are neutral, inert and do not support biological activity,
5. modify the surface energy properties of oral cavity surfaces such that it is more difficult for food particles, cellular debris and various plaque precursors and formers to attach to these oral cavity surfaces, 6. form a fugitive thin, transparent coating that contains surfactant, disrupts plaque and does not build up on oral cavity surfaces and is removed by the normal clearing and flushing action of the mouth usually within about 30 minutes,
7. impart a pleasant "smooth" feeling to the surfaces of the mouth, gums and teeth, described as "conditioned", and
8. retain various flavors, sweeteners and pharmacologically preparations active on surfaces of the mouth imparting an unexpected prolonged effect of the pharmacologically active substances as well as prolonged flavor perception.

The mouth conditioning and coating substances include: various silicones, long chain hydrocarbons, carbowaxes and polymers such as:

silicone glycol co-polymers,
polydimethyl siloxanes,
long chain hydrocarbons, especially normal paraffins having a chain length of 16 carbon atoms or greater, paraffins with several loci of branching and unsaturation, where the extent of such branching and unsaturation does not create unacceptable toxicity nor lower the solidification point below body temperature, Carbowaxes (polyethylene glycols), and polymers which have limited solubility in ethanol and water solutions where the ethanol; water ratio is greater than 0.3:1 but have essentially no solubility in water or saliva at lower ratios.

The combination of certain cleaners in high concentrations with certain mouth conditioning and coating substances, wherein the latter is emulsified via a "hot-melt" emulsion in the form, in a non-irritating, microbiologically stable, alcohol-free rinse is novel. The disruptive cleaning and plaque disruption obtained with this combination in the mouth, is novel.

Furthermore, the cleaner, coating substance, and saliva or gingival crevice fluid mixture obtained when the compositions are introduced into the mouth are ingestible and can be pleasantly swallowed, if necessary, which further distinguishes it from typical oral rinse and pre-rinse compositions containing alcohol. For example, unlike typical cleaners used in dentifrices and rinses the cleaners of the present invention do not fill the mouth with foam and can be pleasantly swallowed. The pre-rinse of the present invention need not be rinsed from the mouth after use with a water rinse. This allows the cleaners and conditioners which are somewhat substantive to continue to disrupt plaque matrix formation. It is unexpected that the compositions of the invention can disrupt plaque formation without resort to antimicrobial ingredients. (see, contra. U.S. Pat. No. 4,657,758). The various surfaces of teeth and gums are coated with a smooth thin film and surfactant which remains for extended periods and prolongs this disruptive effect on plaque matrix formation.

Surprisingly, the cleaning and/or coating compositions of the present invention retain good surface active properties, are low foaming and are able to clear the mouth of cell debris, food debris, material alba, sugars, starches and other precursors to plaque. Additionally, the unexpected high levels of surfactant achievable with the preparations of the present invention, e.g., from about 2 to 50 times greater than most commercial rinses, pre-rinses and dentifrices, are disruptive to the material alba present as well as the physical integrity of the plaque matrix. This disruptive cleansing removes more debris while softening the plaque matrix and renders the plaque matrix more easily removable by brushing. This disruptive effect surprisingly is obtained with minimal foaming (considering the high concentrations of cleaners) while simultaneously coating the oral cavity surfaces with a thin neutral film containing the surfactant and flavorants of the compositions. This neutral fugitive film is not metabolizable by resident oral cavity microorganisms.

By contrast, natural film formers such as lecithin-containing substances are known to form anti-attachment films on mouth surfaces but these films are not suitable for the purposes of the present invention since they are metabolizable and are not neutral. Most of these naturally occurring coating substances support biological activity rather than form non-supportive inert films and as such, work opposite to the suitable film formers of the present invention. See for example: Menaker, "The Biologic Basis of Dental Caries", Chapter 16; Gibbons and Hoote, *Ann. Rev. of Microbiology.* Vol. 29, pp. 119–44; and Hayes, *J. Dent. Res.,* Vol. 632, pp. 2–5 (1984).

As long as the transient inert coating of the present invention remains, it:
1. continues to support a disruptive effect on the plaque
2. reduce retained material alba,
3. conditions gums and teeth,
4. restricts the subsequent adherence of plaque forming materials to the teeth, thus continuing the disruption of plaque formation;
5. continues to impart a "smooth" feeling to the mouth, and
6. prolongs the flavor perception of the oral rinse preparation.

These features are described in various Examples below. The prolonged flavor perception, described as a "clean, just-brushed feeling" confirms the various prolonged effects and is particularly novel and unexpected which makes rinsing a more pleasant experience. This has a positive effect on patient compliance.

Most users of the oral hygiene preparation of the present invention perceive a quite different feeling in the mouth than is perceived with typical rinses and pre-rinses. For example:
1. there is no alcohol bite and/or irritation,
2. the mouth feels exceptionally clean and smooth and the surfaces of the teeth are slick and shiny. This well lubricated feeling of the mouth is particularly beneficial to mouth breathers and those afflicted with mouth dryness,
3. the prolonged flavor perception is generally described as "freshness" and persists much longer with the compositions of the present invention than when the same flavor is introduced into the mouth in the form of a traditional dentifrice and/or mouth rinse or pre-rinse. This residual flavor benefit is an important element contributing to the perceived efficacy of the products, i.e., the user perceives that the combination is "doing something" in the mouth. This perceived signal of efficacy reinforces user compliance a key element in maximizing the efficacy of the present invention.

Combining the various disruptive, cleaning, coating, mouth-feeling benefits of the compositions of the invention into an alcohol-free rinse provides for the first time, a commercializable rinse product that controls plaque formation and clears the mouth of debris without killing germs and/or altering the microflora of the mouth. The absence of the alcohol-burn and bite is appealing to those with sensitive or irritated mouths, those suffering from gingivitis and to those who do not prefer the alcohol taste or cannot tolerate even low quantities of alcohol for personal health reasons as well as to children who for safety reasons are precluded from present commercial products.

Frequency of rinsing is encouraged by the unique characteristics of the present invention. These cause the user to return to the invention regularly, stimulated as much by the pleasant experience as by conscious recall of "my mouth needs rinsing". These characteristics are: the product is exceptionally pleasant to use. The various flavors and conditioners in the compositions of the present invention are formulated to be as pleasant as a good quality candy mint and to contribute this pleasant taste over a longer-than-expected time period thus enhancing the "its working" perception. The feeling in the mouth is equally pleasant. A smooth, tingly "something's happening" feeling is perceived immediately upon rinsing, followed by a clean, fresh, well lubricated mouth and tooth surfaces which unexpectedly persists much longer than mints, gums, breath fresheners and traditional alcohol-containing mouth rinses and toothpastes.

In addition to the cleaning and/or coating compositions described above, preferred embodiments of the present invention use various viscosity control agents to impart certain viscosity characteristics to the products of the invention. It is believed that in these preferred embodiments of the invention, viscosity plays a role in achieving optimum mouth feel and flavor retention characteristics of the invention. A viscosity ranging between about 2 and about 15 cps is preferred and between about 3 and about 12 cps is particularly preferred.

Viscosity control agents which are known in the food and consumer products, can be selected from natural and synthetic gums such as: carragenan, gum tragacanth, methyl celluloses and derivatives thereof such as hydroxyethyl methyl cellulose, polyvinyl pyrrolidone, and hydrophylic carboxyvinyl polymers such as those sold under the trademark Carbopol 934. Generally, about 0.01 percent to about 10 percent of one or more viscosity control agents is used, see Table I.

The pre-rinse preparations of the present invention generally contain:
a. from between about 75 and about 99 percent preferably from between about 80 and about 97 percent by weight water,
b. from between about 1 and about 5, preferably from between about 1.5 and 3.0 percent by weight of surfactant, and
c. from between about 0.001 and about 0.5, preferably from between about 0.005 and about 0.2% by weight of a coating substances emulsified in said surfactant. The ratio of surfactant to coating composition can range from between about 1 to 0.001 and about 4 to 0.5 preferably from between about 1.5 to 0.005 and about 2.5 to 0.2% by weight.

The compositions of the invention may also contain certain phosphate salts, such as sodium or potassium pyrophosphates, or mixtures thereof, which have been shown to aid in the control of plaque and the calcified plaque called tartar.

The preparation of the invention may also contain a desensitizing agent which is particularly useful for sensitive teeth and gums, irritated gums and/or gums that are healing from surgery. Suitable desensitizing agents include strontium chloride and potassium nitrate.

The oral pre-rinse emulsions of the present invention may also contain various anti-caries substances such as various fluoride containing agents including: sodium fluoride, ammonium fluoride, an amine fluoride (Olaflur 297) fluorophosphates, etc. The coating compositions tend to hold these fluoride substances in intimate contact with the surfaces of the teeth thereby assuring the fluoride ions exchange with the enamel.

In addition to the stabilizers, flavoring and pH buffering ingredients; the compositions of the invention can optionally contain at least one humectant such as glycerin, xylitol, sorbitol, hydrogenated glucose syrup and propylene glycol. Generally, such humectants are utilized in the proportion of about 0.1 percent to about 25 percent by weight based upon the total weight of the composition. Preferably, the humectant is utilized in an amount of about 3 to 15 percent by weight, see Examples below.

Flavors, colorants, sweeteners, non-cariogenic sugars and humectants are also used to impart optimum cosmetic characteristics to the composition of the present invention.

Generally, the flavoring component is present as an oil, emulsified into the composition by the surfactant component.

The conventional flavoring components are exemplified by the following materials, menthol, anise oil, benzaldehyde, bitter almond oil, camphor, cedar leaf oil, cinnamic aldehyde, cinnamon oil, citronella oil, clove oil, eucalyptol, heliotropin, lavender oil, peppermint oil, phenyl salicylate, pine oil, pine needle oil, rosemary oil, sassafras oil, spearmint oil, thyme oil, thymol, wintergreen oil, lemon and orange oils, vanillin, spice extracts and other flavoring oils generally regarded as safe (GRAS) by health authorities.

Additional adjuvants can be added to provide color, flavor, or sweetening effects, as desired. Examples of suitable sweetening agents include sorbitol, sodium cyclamate, saccharine, commercial materials such as the Nutrasweet ® brand of aspartame and xylitol. Citric acid or acetic acid is often utilized as a flavor additive. All types of flavoring materials are generally used in amounts of about 1.0 to about 20 percent by weight, preferably about 2.0 percent to about 15 percent by weight.

A buffering ingredient may also be added to the compositions of the present invention in order to prevent natural degradation of the flavoring components or therapeutically active ingredients. Generally, the pH of these compositions is adjusted from about 4.0 to about 7.0 depending on the chemistry of the active ingredient most requiring protection. The buffering ingredients such as an alkali metal salt of a weak organic acid, for instance, sodium bicarbonate or potassium tartrate is generally added in an amount of about 0.1 to about 1.0 percent by weight. Other buffering agents such as weak organic acids or salts or weak bases and strong acids such as boric acid, citric acid, ammonium chloride, etc. can also be used in similar concentrations.

Microbiological stabilizers are often added to the compositions for additional control, such as:
a. sodium benzoate, sodium or potassium sorbate, methyl paraben, propyparaben and others approved for ingestion,
b. chemical oxidative control substances, such as ethylene-diaminetetracetic acid, BHA, BHT, propyl gallate and similar substance approved for ingestion. Concentration levels of these stabilizers comply with industry and regulatory standards.

EXAMPLES

The following examples provide a synopsis of dental and oral hygiene preparations combined according to the invention in an alcohol-free pre-rinse or rinse formulation and show the unexpected results obtained by the use of the compositions disclosed herein. The examples are intended for the purpose of illustration and are not to be construed as limiting in any way.

The water used in each formulation was deionized. The various ingredients were mixed using the blending practice described below.

In Tables I and II below the percent by weight of each component is listed immediately after the component.

Most of the preferred surfactants of the invention are solid at room temperature. In contrast, the coating composition in these oral rinse preparations may be either liquid or solid in the surfactant phase or the water phase. Additionally, other components such as flavor oils have limited water solubility and are usually not soluble in the surfactant phase. A "Hot-melt" emulsion process is the preferred manufacturing method used to prepare the various preferred embodiments of the present invention.

TABLE I

| Example | Surfactant (a) Concentration | Silicone (b)(c)(d) Concentration | Flavor (e)(f)(g)(h) Concentration | Sorbitol/ Glycerin Humectant Concentration | Methocel/ Carragenan Viscosifier Concentration | Sodium Saccharin Concentration |
|---|---|---|---|---|---|---|
| 1 | (a)(1.0) | (b)(0.1) | (e)(.3) | 2/1.0 | .1/0 | .1 |
| 2 | (a)(2.0) | (b)(0.1) | (e)(.3) | 8/2 | .2/0 | .1 |
| 3 | (a)(2.0) | (b)(0.2) | (e)(.3) | 8.6/2 | .2/0 | .1 |
| 4 | (a)(2.0) | (b)(0.8) | (e)(.3) | 8/3 | .2/.1 | .1 |
| 5 | (a)(2.0) | (b)(0.8) | (f)(.4) | 13/3 | .2/.1 | .1 |
| 6 | (a)(2.0) | (b)(0.8) | (g)(.4) | 20.8/3 | .2/.1 | .1 |
| 7 | (a)(2.0) | (b)(0.8) | (e)(.3) | 8/3 | .2/.1 | .1 |
| 8 | (a)(2.0) | (b)(0.8) | (e)(.3) | 8/3 | .2/.1 | .1 |
| 9 | (a)(2.0) | (b)(0.8) | (e)(.3) | 8/3 | .2/.1 | .1 |
| 10 | (a)(2.0) | (c)(0.2) | (e)(.3) | 8/3 | .2/.1 | .1 |
| 11 | (a)(2.0) | (c)(.005) | (e)(.3) | 8/3 | .2/.1 | .1 |
| 12 | (a)(2.0) | (d)(.2) | (e)(.3) | 8/3 | .2/.1 | .1 |
| 13 | (a)(2.0) | (d)(.005) | (e)(.3) | 8/3 | .2/.1 | .1 |
| 14 | (a)(2.0) | (c)(.005) | (h)(.2) | 8/3 | .2/.1 | .1 |
| 15 | (a)(2.0) | (c)(.005) | (h)(.2) | 8/3 | .2/.1 | .1 |

| Example | Sodium Benzoate Preservative Concentration | Citric Acid Buffer pH | FD&C Color Number Concentration | Water Concentration |
|---|---|---|---|---|
| 1 | — | — | #33(1.0) | 94.4 |
| 2 | — | — | #33(1.0) | 87.3 |
| 3 | — | — | #33(1.0) | 86.6 |
| 4 | — | — | #33(1.0) | 83.5 |
| 5 | (i) | — | #6(1.0) #4(1.0) | 78.2 |
| 6 | (i) | — | #1(.06) #33(.34) | 73.6 |
| 7 | .3 | 4.0 | #33(1.0) | 84.3 |
| 8 | .3 | 5.0 | #33(1.0) | 84.3 |
| 9 | .3 | 5.5 | #33(1.0) | 84.3 |
| 10 | (.25) | 5.0 | #33(1.0) | 82.8 |
| 11 | (.25) | 5.0 | #33(1.0) | 83.0 |
| 12 | (.25) | 5.0 | #33(1.0) | 82.8 |
| 13 | (.25) | 5.0 | #33(1.0) | 83.0 |
| 14 | (.1) | 5.0 | #33(1.0) | 83.5 |
| 15 | (.3) | 5.0 | #33(1.0) | 83.3 |

TABLE II

| Example | Surfactant (a)(j)(k) (o)(p)(q)(r) Concentration | Silicone (c)(d)(l) (m)(n) Concentration | Flavor (e) Concentration | Sorbitol/ Glycerin Humectant Concentration | Methocel/ Carragenan Viscosifier Concentration | Sodium Saccharin Concentration |
|---|---|---|---|---|---|---|
| 16 | (a)(.5) | (c)(.01) | (e)(.3) | 5/1 | 0/.2 | .2 |
| 17 | (a)(3.0) | (d)(.1) | (e)(.3) | 20/4 | — | — |
| 18 | (j)(2.0) | (l)(.1) | (e)(.3) | 10/2 | .3/0 | .2 (aspartame) |
| 19 | (j)(2.0) | (m)(.05) | (e)(.3) | 10/2 | .3/0 | .1 |
| 20 | (k)(1.0) | (n)(.1) | (e)(.3) | 10/2 | .3/0 | .1 |
| 21 | (o)(2.0) | (d)(.02) | (e)(.3) | 10/2 | — | .1 |
| 22 | (p)(1.0) | (d)(.01) | (e)(.3) | 10/2 | — | .1 |
| 23 | (q)(2.0) | (d)(.05) | (e)(.3) | 10/2 | 0/.1 | .1 |
| 24 | (r)(1.5) | (d)(.015) | (e)(.3) | 10/2 | .1/0 | .1 |

Potassium/ Sorbate Sodium Benzoate    Citric    FD&C Color

TABLE II-continued

| Example | Preservative Concentration | Acid Buffer pH | #33 Concentration | Water Concentration |
|---|---|---|---|---|
| 16 | .1/.1 | 5.0 | 1.0 | 91.6 |
| 17 | .3/.3 | 5.0 | 1.0 | 71.0 |
| 18 | .3/.3 | 5.0 | 1.0 | 83.5 |
| 19 | .3/.3 | 5.0 | 1.0 | 83.6 |
| 20 | .3/.3 | 5.0 | 1.0 | 84.6 |
| 21 | .3/.3 | 5.0 | 1.0 | 83.3 |
| 22 | .3/.3 | 5.0 | 1.0 | 84.3 |
| 23 | .3/.3 | 5.0 | 1.0 | 83.4 |
| 24 | .3/.3 | 5.0 | 1.0 | 83.7 |

FOOTNOTES TO TABLE I & II
(a)Pluronic F-127 (BASF)
(b)AF Emulsion, 30% polydimethyl siloxane (Dow Corning)
(c)#200, 100% polydimethyl siloxane, (Dow Corning)
(d)#1500, anti-foam Dow Corning #200 with silica gel added.
(e)IFF-101 a proprietary vanilla mint flavor oil
(f)IFF-343 a proprietary orange mint flavor oil
(g)IFF-638 a proprietary grape flavor oil
(h)Mixture of IFF-101 (3 parts) and IFF-082 (1-part) gentlemint oil
(i)Preservatives, propyl paraben (0.05) and methyl paraben (0.15)
(j)Pluronic F-108 (BASF)
(k)S-40K polyethylene glycol stearate (MAZER)
(l)C-22, normal paraffin hydrocarbons, predominately 22 carbons
(m)PEG-2000 polyethylene glycol, molecular weight 2000
(n)#556 silicone-glycol copolymer Dow Corning 556
(o)Pluronic F-127 (BASF) (1 part)
Pluronic L-35 (BASF) (3 parts)
(p)Pluronic F-127 (BASF) (1 part)
Pluronic L-63 (BASF) (3 parts)
(q)Pluronic F-127 (BASF) (3 parts)
Pluronic F-77 (BASF) (1 part)
(r)Pluronic F-127 (BASF) (3 parts)
Pluronic F-87 (BASF) (1 part)

The various examples described above in Tables I and II can be prepared as follows:

In a heated bath, the surfactant is melted and maintained at approximately 10° C. above its melting point, or at a temperature that does not adversely effect the addition of other ingredients to the melt; while maintaining a viscosity sufficiently low for processing.

The coating compositions of the invention are emulsified into the surfactant melt with high shear agitation, or by inducing shear via continuous apparatus such as homogenizers or colloid mills. Various air containing solids such as silica or oil soluble weighting agents such as brominated vegetable oils can be employed to adjust the specific gravity of the coating agent, thereby assuring a stable oral rinse preparation substantially free from layering or "ringing out".

The "hot-melt" emulsion is maintained in the molten state and re-emulsified with the other non-water soluble substances including flavor oils. Flavor oils containing substantial quantities of solids such as menthol, can be melted prior to emulsifying. Flavor oils can also be weighted if necessary, as described in 2 above. It is preferred to include antioxidants and/or chelating agents required for various flavor oils into the oil phase such as BHA, BHT, propyl gallate and EDTA.

Prior to the addition of viscosifiers to the composition of the invention, the viscosifiers are predispersed by mixing them with water soluble but low water activity liquids such as Sorbitol-70, glycerin, etc. This predispersion allows for the uniform distribution of the viscosifier particles into the water phase resulting in more uniform hydration.

Final blending is preferably accomplished by adding the various phases into a high shear mixer preferably equipped with de-aeration means in the following sequence, a. various water soluble components are added to the requisite amount of water, including colorants, sweeteners, preservatives, buffering agents, etc.,
b. pre-dispersed viscosifiers are added, and
c. the molten emulsion is added preferably using a colloid mill.

DISCUSSION OF "USE" RESULTS

Each Example 1 through 15 worked as well as, or better than commercial oral rinses, but had unique properties as described below.

In Example 1, the viscosity was lower than Examples 2 and 3, without the natural mouth feel of Example 4. The desired "clean mouth feel" is not as pronounced and the sweetness was deemed "artificial."

In Example 2, the formulation showed good perception of cleaning during use, with less clean mouth perception after expectorating compared to Examples 3 and 4.

The Example 3 formulation showed better mouth feel than the formulations of Examples 1 or 2.

The Example 4 formulation showed a large increase in the natural and cleaning perception while in use. After expectorating a clean, smooth feeling is perceived. There was no irritation; no burning sensation. A lasting freshness in the mouth was perceived for about 30 minutes. The mouth surfaces feel "conditioned" after using this formulation. This was perceived as prolonged "disruptive cleaning".

With the formulations of Examples 5 and 6, both examples demonstrate the surprising retention of the flavor characteristics in spite of high surfactant content. Example 5 is a fruity orange flavored formulation, with a cooling, mint perception after expectorating. This Example was preferred for children. When tested for microbial stability, further microbial growth was prevented but the microbial count was not reduced below the original inoculum, as seen in Table III, Example 14 and 15.

Examples 7 to 9 contained slightly higher level of sodium benzoate than normally used for preservation purposes but much less than required for an oral antimicrobial effect. Examples adjusted to various pH levels in order to demonstrate the effect on overall mouth feel and taste. At pH 4.0 none of the soapy note associated with surfactants and sodium benzoate was perceived. However, the sharp, sour taste was inconsistent with the mint flavor used. Fruit flavors are suggested here. At pH 5.5 a slight soapy perception was noted, pH 5.0 is preferred and is sufficiently acid to insure optimum preservative action of the sodium benzoate Examples 10 to 13. Examples 10 and 12 are opaque, with a smooth mouth feel with excellent retention of the just brushed feeling. It is noted Example 12 requires less shear to provide suitable distribution of the second phase. Example 11 is clear and surprisingly the mouth feel attributable to the silicone is still present at this ratio of silicone to surfactant. Example 13 is perceived similar to Example 11 except that it has a slightly cloudy visual appearance.

The Examples described in Table III below establish the microbial stability of the pre-rinse, rinse compositions of the invention. Microbial stability was obtained after 30 days at 37° F. with sodium benzoate concentrations of 0.1 and 0.3% respectively.

TABLE III

| Example # from Table II | Sodium Benzoate % by wt. | Initial | | After 30 Days | |
|---|---|---|---|---|---|
| | | pH | Innoculum* CFU/ml | pH | CFU/ml |
| 14 | 0.1 | 5.0 | $10^8$ | 5.0 ± .1 | 100 |
| 15 | 0.3 | 5.0 | $10^8$ | 5.0 ± .1 | 100 |

*innoculum:
$10^8$ ml of each of the following:
*Escheridia coli*
*Pseudomonas Aeruginosa*
*Staphylococcus Aureus*
*Aspergillis Niger*

DISCUSSION OF TABLE IV

For the purposes of the present invention, the Oral Cavity Residence Factor (OCRF) is defined as the summed hedonic response (competing pleasure and pain perception) expressed as:

$$\frac{\text{Voluntary Retention Time}}{10} \text{ (sec.)} \times \text{Urge to Rinse}$$

which is established as follows:

A. At least ten subjects, preferably equal numbers of men and women are tested. The subjects qualify as follows:
  Adults,
  No oral mucosa irritations,
  No canker sores,
  No periodontal pockets deeper than 3 mm, and
  No oral cavity cuts, bruises or other abnormalities, B. Each subject is asked to introduce 15 ml of the test material into their oral cavity and flush the liquid vigorously throughout the mouth with a "swishing", rinsing motion for as long as the test material is comfortable to their mouth, teeth, gums and tongue. Each subject is instructed to expectorate. The voluntary retention time is measured by a stop watch and starts when the test material is introduced into the mouth and concludes upon expectoration.

C. Immediately upon expectorating, each subject is asked to determine their urge to rinse with water on a scale of 1 to 10 where 1 equals "urgently, as soon as possible" and 10 is "no urge to rinse". The average or mean OCRF for the test subjects is determined for each test material, per the equation set out above.

The OCRF for two samples of the present invention from Table I, i.e., Examples 10 and 11, were determined along with that of two commercial products, Plax ® Pre-Rinse and Listerine ® mouthwash. The results are set forth in Table IV below. Note, 11 test subjects were qualified, five women and six men. All four products were tested with all subjects during a single test period.

TABLE IV

| Product Tested | Alcohol Content % by wt. | Silicone Content % by wt. | OCRF |
|---|---|---|---|
| Example 10 from Table I | 0.0 | 0.2 | 16.52 |
| Example 11 from Table I | 0.0 | 0.005 | 15.52 |
| Listerine Mouth Rinse | 27. Approx. | 0.0 | 1.28 |
| Plax Pre-Rinse | 6.95 | 0.0 | 12.44 |

The results shown in Table IV establish that the products of the present invention can be retained in the oral cavity for substantially longer periods than the leading commercial pre-rinse and the leading commercial mouthwash.

For example, the OCRF of Example 10 is 33% greater than Plax ® Pre-Rinse and 1290% greater than Listerine ® mouthwash. The OCRF of Example 11 is 25% greater than Plax ® Pre-Rinse and 2112% greater than Listerine ® mouthwash. This latter comparison further emphasizes the influence of alcohol concentration on retention time of the rinse in the mouth.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A substantially clear, freeze-thaw and elevated temperature stable, alcohol-free, oral rinse composition consisting essentially of water and an emulsion of a surfactant and a mouth conditioner, which is:
  non-irritating,
  alcohol-free
  low-foaming, and
  microbiologically stable, having:
    a. a pH from between about 4 and about 7
    b. a viscosity greater than about 1 cps, and
    c. an oral cavity residence factor from between about 12 and about 20,
  containing:
    a. a surfactant in a concentration sufficient to achieve a plaque matrix disrupting effect without altering appreciably the critically balanced microflora of the oral cavity, and
    b. a mouth conditioner emulsified in said surfactant;
  wherein
    a. the concentration of surfactant is from between about 1 and about 5% by weight,
    b. the concentration of mouth conditioner is from between about 0.001 and about 0.8% by weight, and
    c. the ratio of surfactant to conditioner is from between about 1000:1 and about 10.1;

and wherein:
the surfactant is selected from the group consisting of polyethylene glycol stearate, polyethylene glycol monostearate, coconut monoglyceride sulfonates, block copolymers of polyoxyethylene and polyoxybutylene, allylpolyglycol ether carboxylates, polyethylene derivatives of sorbitan esters, propoxylated cetyl alcohol, block copolymers comprising a congeneric mixture of conjugated polyoxybutylene and polyoxylethylene compounds having as a hysdrophobe a polyoxybutylene polymer of at least 1200 molecular weight, and mixtures thereof; the mouth conditioner emulsified in said surfactant is selected from the group consisting of: silicones, silicone glycol co-polymers, polydimethyl siloxanes, long chain hydrocarbons, normal paraffins having a chain length of 16 carbon atoms or greater, paraffins with several loci of branching and unsaturation and carbowaxes, such that said alcohol-free oral rinse fights plaque via a non-invasive, plaque disrupting mechanism.

2. The oral hygiene composition according claim 1, wherein the composition contains sufficient water to be suitable for use as a pre-rinse.

3. The oral hygiene composition according to claim 2, wherein the pH of the pre-rinse is between about 4.5 and 6.0.

4. The oral hygiene composition according to claim 2, wherein the viscosity of the pre-rinse is between about 2 and about 15 cps.

5. The oral hygiene composition according to claim 3, wherein the oral cavity residence factor of the pre-rinse is at least about 15.

6. The oral hygiene composition according to claim 2, wherein the surfactant is a block copolymer of polyoxyethylene and polyoxybutylene.

7. The oral hygiene composition according to claim 6, wherein the concentration of the surfactant is from between about 1.5 and about 2.5% by weight.

8. The oral hygiene composition according to claim 2, wherein the mouth conditioner is a polydimethyl siloxane.

9. The oral hygiene composition according to claim 8, wherein the concentration of mouth conditioner is between about 0.05 and about 0.2% by weight.

10. The oral hygiene composition according to claim 2, wherein the surfactant is a block copolymer of polyoxyethylene and polyoxybutylene at 2.0% by weight and the mouth conditioner is a polydimethyl siloxane at 0.005% by weight, and wherein the composition is substantially clear when visually inspected.

11. The oral hygiene composition according to claim 2, wherein the surfactant is a block copolymer of polyoxyethylene and polyoxybutylene at 2.0% by weight and the mouth conditioner is a polydimethyl siloxane at 0.2% by weight, and wherein the composition is substantially opaque when visually inspected.

12. The oral hygiene composition according to claim 7, further containing from between about 0.1 and about 0.5% by weight of one or more flavor materials emulsified in said surfactant, and wherein the flavor materials are insoluble in the mouth conditioner.

13. The oral hygiene composition according to claim 2, further containing in the aqueous phase materials selected from the group consisting of sugars, artificial sweeteners, preservatives, viscosifiers, buffering agents and antioxidants.

14. The oral hygiene composition according to claim 1, wherein said composition suitable for use as a rinse.

15. The oral hygiene composition according to claim 14, wherein the pH of the rinse is between about 4.5 and about 6.0.

16. The oral hygiene composition according to claim 14, wherein the viscosity of the rinse is between about 2 and about 15 cps.

17. The oral hygiene composition according to claim 14, wherein the oral cavity residence factor of the rinse is at least about 15.

18. The oral hygiene composition according to claim 14, wherein the surfactant is a block copolymer of polyoxyethylene and polyoxybutylene.

19. The oral hygiene composition according to claim 18, wherein the concentration of the surfactant is from between about 1.5 and about 2.5% by weight.

20. The oral hygiene composition according to claim 14, wherein the mouth conditioner is a polydimethylsiloxane.

21. The oral hygiene composition according to claim 20, wherein the concentration of mouth conditioner is from between about 0.005 and about 0.2% by weight.

22. The oral hygiene composition according to claim 14, wherein the surfactant is a block copolymer of polyoxyethylene and polyoxybutylene at about 2.0% by weight and the mouth conditioner is a polydimethyl siloxane at about 0.005% by weight, and wherein the composition is substantially clear when visually inspected.

23. The oral hygiene composition according to claim 19, wherein the surfactant further contains from between about 0.1 and about 0.5% by weight of one or more flavor materials emulsified therein, and wherein the flavor materials are insoluble in the mouth conditioner.

24. The oral hygiene composition according to claim 14, further containing in the aqueous phase, one or more additional ingredients selected from the group consisting of sugars, artificial sweeteners, preservatives, viscosifiers, buffering agents and antioxidants.

25. The oral hygiene composition according to claim 14, wherein the surfactant is a block copolymer of polyoxyethylene and polyoxybutylene at about 2.0% by weight and the mouth conditioner is a polydimethyl siloxane at about 0.2% by weight, and wherein the composition is substantially opaque when visually inspected.

26. The oral hygiene composition according to claim 14, wherein the surfactant is selected from the group consisting of polyethylene glycol stearate, polyethylene glycol monostearate, coconut monoglyceride sulfonates, block copolymers of polyoxyethylene and polyoxybutylene, allylpolyglycol ether carboxylates, polyethylene derivatives of sorbitan esters, propoxylated cetyl alcohol, block copolymers comprising a cogeneric mixture of conjugated polyoxybutylene and polyoxylethylene compounds having as a hydrophobe a polyoxybutylene polymer of at least 1200 molecular weight, and mixtures thereof, and the mouth conditioner emulsified in the surfactant is selected from the group consisting of silicones, silicone glycol co-polymers, polydimethyl siloxanes, long chain hydrocarbons, normal paraffins having a chain length of 16 carbon atoms or greater, paraffins with several loci of branching and unsaturation and carbowaxes.

27. A method of treating the oral cavity to reduce plaque; clear the mouth of debris; and condition both the teeth and gums without disrupting the critically balanced microflora of the oral cavity, comprising rinsing or pre-rinsing the oral cavity with an alcohol free oral hygiene composition consisting essentially of an aqueous emulsion that is:
  non-irritating,
  alcohol-free
  low-foaming, and
  microbiologically stable, having:
    a. a pH from between about 4 and about 7,
    b. a viscosity greater than about 1 cps, and
    c. an oral cavity residence factor from
  between about 12 and about 20, containing:
    a. a surfactant in a concentration sufficient to achieve a plaque matrix disrupting effect, without altering appreciably the critically balanced microflora of the oral cavity, and
    b. a mouth conditioner emulsified in said surfactant;
  wherein:
    a. the concentration of surfactant is from between about 1 and about 5% by weight,
    b. the concentration of mouth conditioner is from between about 0.001 and about 0.8% by weight, and
    c. the ratio of surfactant to conditioner is from between about 1000:1 and about 10.1.

28. The method according to claim 27, wherein the surfactant is selected from the group consisting of polyethylene glycol stearate, polyethylene glycol monostearate, coconut monoglyceride sulfonates, block copolymers of polyoxyethylene and polyoxybutylene, allylpolyglycol ether carboxylates, polyethylene derivatives of sorbitan esters, propoxylated cetyl alcohol, block copolymers comprising a cogeneric mixture of conjugated polyoxybutylene and polyoxylethylene compounds having as a hydrophobe a polyoxybutylene polymer of at least 1200 molecular weight, and mixtures thereof, and
  the mouth conditioner emulsified in said surfactant is selected from the group consisting of silicones, silicone glycol co-polymers, polydimethyl siloxanes, $C_{12}$–$C_{24}$ hydrocarbons, normal paraffins having a chain length of 16 carbon atoms or greater, paraffins with several loci of branching and unsaturation and carbowaxes.

29. The method according to claim 27, wherein the pH of the composition is from between about 4.5 and 6.0.

30. The method according to claim 27, wherein the viscosity of the composition is between about 2 and about 15 cps.

31. The method according to claim 27, wherein the oral cavity residence factor of the composition is at least about 12.

32. The method according to claim 27, wherein the surfactant is a block copolymer of polyoxyethylene and polyoxybutylene.

33. The method according to claim 32, wherein the concentration of the surfactant is from between about 1.5 and about 2.5% by weight.

34. The method according to claim 27, wherein the mouth conditioner is a polydimethyl siloxane.

35. The method according to claim 34, wherein the concentration of mouth conditioner is from between about 0.005 and about 0.2% by weight.

36. The method according to claim 27, wherein the surfactant a block copolymer of polyoxyethylene and polyoxybutylene at about 2.0% by weight and the mouth conditioner is a polydimethyl siloxane at about 0.005% by weight.

37. The method according to claim 27, wherein the pre-rinse composition is opaque, the surfactant is a block copolymer of polyoxyethylene and polyoxybutylene at about 2.0% by weight and the mouth conditioner is a polydimethyl siloxane at about 0.2% by weight.

38. The method according to claim 33, wherein the surfactant contains from between about 0.1 and about 0.5% by weight flavor emulsified therein, and wherein the flavor is insoluble in the mouth conditioner.

39. The method according to claim 27, wherein the pre-rinse composition contains, in the aqueous phase, additive ingredients selected from the group consisting of sugars, sweeteners, preservatives, viscosifiers, buffering agent and antioxidants.

40. A method of manufacturing an alcohol-free rinse or pre-rinse emulsion useful in the oral cavity to reduce plaque; clear the mouth of debris; and condition both the teeth and gums without disrupting the critically balanced microflora of the oral cavity; said method comprising emulsifying a mouth conditioner into a molten surfactant with high shear agitation, wherein the resulting aqueous emulsion is:
  non-irritating,
  alcohol-free
  low-foaming, and
  microbiologically stable, having:
    a. a pH from between about 4 and about 7,
    b. a viscosity greater than about 1 cps, and
    c. an oral cavity residence factor from between about 12 and about 20,
  containing:
    a. a surfactant in a concentration sufficient to achieve a plaque matrix disrupting effect, without altering appreciably the critically balanced microflora of the oral cavity, and
    b. a mouth conditioner emulsified in said surfactant;
  wherein:
    a. the concentration of surfactant is from between about 1 and about 5% by weight,
    b. the concentration of mouth conditioner is from between about 0.001 and about 0.8% by weight, and
    c. the ratio of surfactant to conditioner is from between about 1000:1 and about 10.1.

41. The method according to claim 40, wherein the surfactant is selected from the group consisting of: polyethylene glycol stearate, polyethylene glycol monostearate, coconut monoglyceride sulfonates, block copolymers of polyoxyethylene and polyoxybutylene, allylpolyglycol ether carboxylates, polyethylene derivatives of sorbitan esters, propoxylated cetyl alcohol, block copolymers comprising a cogeneric mixture of conjugated polyoxybutylene and polyoxylethylene compounds having as a hydrophobe a polyoxybutylene polymer of at least 1200 molecular weight, and mixtures thereof, and
  the mouth conditioner emulsified in said surfactant is selected from the group consisting of: silicones, silicone glycol co-polymers, polydimethyl siloxanes, long chain hydrocarbons, normal paraffins having a chain length of 16 carbon atoms or greater, paraffins with several loci of branching and unsaturation and carbowaxes.

* * * * *